United States Patent
Eggert et al.

(10) Patent No.: US 11,471,787 B2
(45) Date of Patent: Oct. 18, 2022

(54) TRANSFERRING A TARGET SUBSTANCE BETWEEN TWO LIQUID PHASES

(71) Applicant: RHEINISCH-WESTFÄLISCHE TECHNISCHE HOCHSCHULE (RWTH) AACHEN, Aachen (DE)

(72) Inventors: Armin Eggert, Herzogenrath Nordrhein-Westfalen (DE); Marcel Gausmann, Aachen Nordrhein-Westfalen (DE); Andreas Jupke, Aachen Nordrhein-Westfalen (DE); Tim Massmann, Aachen Nordrhein-Westfalen (DE)

(73) Assignee: RHEINISCH-WESTFAELISCHE-TECHNISCHE HOCHSCHULE, Aachen (DE)

( * ) Notice: Subject to any disclaimer, the term of this patent is extended or adjusted under 35 U.S.C. 154(b) by 173 days.

(21) Appl. No.: 16/959,041

(22) PCT Filed: Jan. 28, 2019

(86) PCT No.: PCT/EP2019/051988
§ 371 (c)(1),
(2) Date: Jul. 28, 2020

(87) PCT Pub. No.: WO2019/145531
PCT Pub. Date: Aug. 1, 2019

(65) Prior Publication Data
US 2020/0360835 A1    Nov. 19, 2020

(30) Foreign Application Priority Data
Jan. 29, 2018  (DE) .......................... 102018000672.8

(51) Int. Cl.
| C07C 51/48 | (2006.01) |
| B01D 11/00 | (2006.01) |
| B01D 9/00  | (2006.01) |
| B01D 11/04 | (2006.01) |

(52) U.S. Cl.
CPC ........ B01D 11/0423 (2013.01); B01D 9/0054 (2013.01); B01D 11/0492 (2013.01); C07C 51/48 (2013.01)

(58) Field of Classification Search
CPC .... C07C 51/48; B01D 11/0419; B01D 9/0054
See application file for complete search history.

(56) References Cited

U.S. PATENT DOCUMENTS

| 3,869,374 | A  | 3/1975  | Goldacker |
| RE32,398  | E  | 4/1987  | DeWitt |
| 4,828,993 | A  | 5/1989  | Sridhar |
| 4,832,813 | A  | 5/1989  | Williamson |
| 5,034,105 | A  | 7/1991  | Berglund |
| 9,057,137 | B2* | 6/2015 | Bhavaraju ............... C25B 13/04 |
| 2004/0262161 | A1 | 12/2004 | Rauls |
| 2006/0169598 | A1 | 8/2006  | Lee |
| 2008/0047838 | A1 | 2/2008  | Van Erkel |
| 2011/0024288 | A1 | 2/2011  | Bhavaraju |
| 2012/0031769 | A1 | 2/2012  | Bhavaraju |

FOREIGN PATENT DOCUMENTS

DE    2062436 A    7/1972

\* cited by examiner

*Primary Examiner* — Sikarl A Witherspoon
(74) *Attorney, Agent, or Firm* — Andrew Wilford

(57) ABSTRACT

The invention relates to a method for transferring a target substance (5), particularly a target molecule (5), between two liquid phases (4, 6; 6, 8; 6, 11), of which at least one phase (4, 6) comprises the target substance (5) to be transferred and at least one phase (4, 8, 11) is an aqueous phase, where at least the aqueous phase (4, 8, 11) is arranged in one of two electrode chambers (1a, 1b, 10a, 10b) which are electroconductively connected, preferably by charge carrier exchange, and separated in terms of the volumes thereof, preferably where the phases (4, 6; 6, 8; 6, 11) are arranged together in one of two electrode chambers (1a, 1b, 10a, 10b) which are electroconductively connected and separated in terms of the volumes thereof, and a pH-value modification is generated by the H and/or OH ions created during the electrolysis in the aqueous phase (4, 8, 11), said modification initiating a transfer process of the target substance (5) between the phases (4, 6; 6, 8; 6, 11). The invention also relates to the use of the method for enrichment and subsequent isolation of the target substance (5).

12 Claims, 3 Drawing Sheets

TRANSFERRING A TARGET SUBSTANCE BETWEEN TWO LIQUID PHASES

CROSS REFERENCE TO RELATED APPLICATIONS

This application is the US-national stage of PCT application PCT/EP2019/051988 filed 28 Jan. 2019 and claiming the priority of German patent application 102018000672.8 itself filed 29 Jan. 2018.

The invention relates to a method of transferring a target substance between two liquid phases. Such a transfer may be intended, for example, for the purpose of extracting or purifying/concentrating the target substance from one of the phases into one of the phases. A target substance may be present as an atom or molecule, for example.

Extraction methods are known in the prior art in which acids or bases are added to the phases in a method steps in order to set the pH values required for extraction.

It is problematic here that significant amounts of salt are produced during separation of a target molecule, and must also be separated and possibly disposed of. Such methods known in the prior art are therefore often uneconomical precisely because of the disposal costs involved. In particular, downstream methods for salt separation, such as nanofiltration, reverse osmosis, etc., may often only be operated economically up to a maximum salt content, and furthermore the recovery of the acids or bases used is also costly.

Such known extraction methods are used, for example, for the purification of fermentatively produced carboxylic acids. The method according to the invention is preferably also intended to be applied in this field but is not limited to this.

Against the background of the problems mentioned above, one object of the invention is to provide a method of transferring a target substance between two liquid phases, in particular a method that may be used for the extraction or purification or concentration of a target substance, such as a fermentatively produced carboxylic acid, in which the use of acids or bases for pH-value adjustment may be dispensed with, thereby eliminating the associated disposal problems. Furthermore, it is preferably an object of the invention to provide a method in which the target substance, preferably the target molecule, may also be obtained as a crystallizate in a preferred embodiment of the method.

In accordance with the invention, the object is attained in that, in the method of transferring a target substance, particularly a target molecule, between two liquid phases, at least one phase comprises the target substance to be transferred and at least one phase is an aqueous phase, wherein at least the aqueous phase is in one of two electrode chambers that are electrically conductively connected, preferably electrically conductively connected by charge carrier exchange, and are separated in terms of the volumes thereof, preferably wherein the phases are arranged together in one of two electrode chambers that are electrically conductively connected and are separated in terms of the volumes thereof, and a pH-value modification is generated by the H and/or OH ions created during the electrolysis in the aqueous phase, this modification initiating a transfer process of the target substance between the phases, in particular when the phases contact or are brought into contact with one another.

The invention may, for example, provide for the arrangement of only the aqueous phase in the electrode chamber and for the pH-value modification to be performed in this chamber by electrolysis, that is to say for example to lower the pH value in an anode chamber or to increase it in a cathode chamber. Only then, for example, may this aqueous phase be brought into contact with the other phase, for example in the electrode chamber or another chamber, after which the transfer process takes place. The transfer process is in this case initiated or brought about by the pH-value modification to such an extent that the transfer of the target substance between the phases would not take place at all or at least only with lower efficiency without the pH-value modification.

Preferably, both phases are arranged simultaneously in the same electrode chamber and are permanently in contact via their interfaces with the pH-value modification occurring in the aqueous phase, which initiates the transfer directly in the electrode chamber.

In the present description, the term "phase" is to be understood in the sense of a homogeneous matter that is separated from another homogeneous matter, in particular that of the other phase, by an interface. The phases are therefore not soluble in each other.

This aqueous phase is, for example, the one from which the target substance, preferably the target molecule, passes into the other phase, this being provided for in particular in a first embodiment of the method. It may also be provided that the aqueous phase is the one into which the target substance, preferably the target molecule, passes from the other phase. This may be provided for in particular in a second embodiment of the method, as described in further detail below. This other phase is preferably a non-aqueous phase.

This electrode chambers together form an electrolysis unit, so that the electrode chambers therefore are formed by an anode chamber and a cathode chamber. Each chamber comprises an inner volume in which the two phases are received. The phases may be filled into the chambers or flow through them. In particular, the method is thus operable batch-wise or also continuously. Furthermore, each chamber comprises an electrode, namely an anode or cathode.

The separation of the volumes in the electrode chambers means that the contents of the chambers, that is to say in particular the phases to which the method is applied, are unable to exchange between the electrode chambers. However, the electrode chambers are certainly connected conductively so that the electrolysis may take place.

The electrode chambers are preferably electrically conductively connected to each other such that charge carrier equalization may take place between the chambers during electrolysis. The chambers are separated, for example, by a semi-permeable chamber wall (diaphragm) or a semi-permeable membrane that is impermeable to the phases but at least allows charge carriers to pass through. Preferably, the separation is carried out in such a way that no diffusive or convective transport of the target substance/molecule against the desired concentration gradient takes place, in particular with the charge equalization being achieved by other charge carriers present in the phases.

Thus, if the transfer of the target substance between two phases is considered in one of the electrode chambers, the other electrode chamber involved in the electrolysis comprises an electrolyte, in the simplest case particularly water, or for example also the aqueous phase of the two phases involved.

This transfer process for transferring the target substance between the two phases may be, for example, a process in which the target substance leaves one phase and dissolves in the other phase.

For example, the invention may provide that, by the aqueous electrolysis taking place between the electrode chambers, the target substance is protonated by the H ions created during the electrolysis or deprotonated by the OH ions created during the electrolysis, the transfer process being formed by the dissolution of the target substance in that of the two phases in which the target substance protonated by the electrolysis or the target substance deprotonated by the electrolysis has the higher solubility. The change in the protonation state of the target substance during electrolysis thus reduces the solubility of the target substance in the phase in which it is initially situated and increases the solubility in the other phase into which it passes.

The invention may also provide that the aqueous electrolysis taking place between the electrode chambers, by the H+ and/or OH⁻ ions formed, initiates the binding of the target substance to a binding partner in one of the phases or the cleaving of the target substance from a binding partner in one of the phases, in particular by pH-value-dependent activation of the binding partner and/or by protonation/deprotonation of the target substance. For example, the binding to the binding partner may be accompanied by protonation of the target substance and/or the cleaving from a binding partner may be accompanied by deprotonation of the target substance.

In this regard, the invention may provide, for example, that the mutually contrary proton reactions are produced in both electrode chambers of an electrolysis unit. This means that in one of the chambers, the anode chamber, a protonation of a target molecule takes place in one phase, while at the same time in another electrode chamber, the cathode chamber, a deprotonation of in particular the same target substance takes place. However, this is not mandatory for the invention.

In an embodiment, for example, a proton production and proton-mediated formation of the bond to the binding partner in one electrode chamber may be electrically connected to the hydroxide ion production and OH-initiated cleaving of the bond between target substance and binding partner in the other chamber. It would also be possible to use only one reaction and to use another half-cell reaction as a counter-reaction (for example production of a base, for example to neutralize an acidic return current of a phase from the anode chamber).

Essential for further understanding is that the target substance under consideration, in particular the molecule under consideration, is described and understood as a target substance/target molecule both in its protonated and deprotonated state.

The essential core concept of the method is based on the fact that water electrolysis in the spatially separated chambers of the electrolysis unit produces H+ and OH⁻ ions, which causes a change in the pH value of the aqueous phase. In this way, the necessary adjustment of the pH value may be achieved by the direct application of an electric current. An external acid or base addition is therefore not necessary, and the associated salt formation is avoided. The separation of the target substance is therefore carried out by a pH-value-dependent or acid-/base-catalyzed extraction. As described later, the invention may also provide for a pH-value-dependent crystallization step that may also be carried out in an electrode chamber.

In the transfer of the target substance, preferably the target molecule between the phases, in at least one of the electrode chambers, the invention preferably provides in all possible embodiments that the phases are dispersed in the electrode chamber while the electrolysis is performed.

For example, the dispersion may be actively operated in the electrode chamber, for example by mixing the phases by moving mixing elements such as a stirrer. The dispersion may also be generated by ultrasound, especially with an ultrasound-generating element within the electrode chamber.

The phases may also be dispersed outside the electrode chamber and introduced into the chamber in a dispersed state. It may be provided that the dispersion is created by the flows inside the chamber or that a previously created dispersion is retained, for example by the flow created by the rising gas bubbles, possibly using passive flow-conducting elements in the chamber.

Such a dispersion is preferably used in all possible method steps in which transfer between two liquid phases takes place.

By mixing and achieving the dispersion, a significant increase in the interface between the phases is provided, enabling the transfer of the target substance/target molecule between the phases with a higher efficiency.

The invention may provide that the phase into which the target substance passes comprises an organic solvent, in particular that this phase is formed by the organic solvent. Such an organic solvent may be selected for example from alcohols, for example octanol, or esters, for example butyl acetate or aliphatic compounds.

This phase may alternatively or additionally comprise or be formed by a pH-value-dependent reactive binding partner. For example, this may be selected from the group of aliphatic amines with at least 10 carbon atoms or organo-phosphoric acids with 2 to 3 alkyl groups.

The target substance is preferably a target molecule, preferably having at least one functional group that gives the substance a pH-value-dependent solubility and/or that may participate in reversible reactions, for example a carboxyl group. The target molecule may be selected, for example, from the group of water-soluble amines, water-soluble amino acids, water-soluble alkanediols and/or water-soluble carboxylic acids.

A preferred embodiment of the invention may provide that a first phase is formed by an aqueous solution of an acid as target molecule and a second phase either comprises a reactive extraction agent as binding partner, in particular this phase is formed from this reactive extraction agent, and/or the second phase comprises an organic solvent, and in particular is formed from the latter, wherein the acid is protonated in the anode chamber of both electrode chambers, and wherein the acid is reactively attached to the reactive extraction agent, in particular by hydrogen bonds, or the acid dissolves in the organic solvent, in which the protonated acid has a higher solubility compared to the deprotonated acid.

When the acid binds to the reactive extraction agent, a complex may be formed, preferably one that dissolves in the second phase.

In both possible cases, the acid is therefore transferred from the first phase into the second phase.

The second phase preferably has a smaller volume in the anode chamber than the first phase. Preferably, this may already lead to a concentration or purification of the target molecule in the second phase compared to the first phase, but this is not mandatory for the invention.

By selecting and setting different pH values, different acids may be selectively separated from each other depending on their pKs value. The setting of the pH value required for a specific acid may be realized, for example, by adjusting the electrolysis capacity and/or residence time.

It is particularly preferred here that the first phase is taken from a fermentation reactor, and in particular that this first phase thus comprises an acid in aqueous solution obtained by fermentation.

Particularly preferably, the method may furthermore provide that, once the target molecule has been transferred to the second phase in accordance with the above-described steps, the first phase is fed to a cathode chamber in which electrolysis is also carried out, and this first phase from which the acid has been extracted is treated by electrolysis and is then returned to the fermentation reactor. For example, the return to the fermentation reactor may be carried out while the electrolysis is being performed or also afterwards. This treatment may also be carried out in batches or continuously, for example in chambers of an electrolysis unit through which the aqueous phase flows in series.

The electrolysis in the cathode chamber causes the pH value of the first phase, which was lowered during extraction, to be raised again. Preferably, this cathode chamber may be one that is electrically associated with the anode chamber where the above-mentioned process is carried out. A cathode chamber and anode chamber always form an electrolysis unit.

A further, second variant of the method may provide that a first phase is formed by a complex of a reactive extraction agent as binding partner and a protonated acid bound thereto, in particular by hydrogen bonds, as target molecule, or a first phase is formed by an organic solvent in which a protonated acid is dissolved and the second phase comprises water, wherein the protonated acid is deprotonated in the cathode chamber of both electrode chambers and is either cleaved from the reactive extraction agent by breaking of the bonds, in particular the hydrogen bonds, preferably thereby dissolving in the aqueous phase, or, if no reactive extraction agent is present, the deprotonated acid dissolves in the aqueous phase. Thus, the acid is transferred here from the first phase into the second phase by dissociation (from the reactive extraction agent) or merely by dissolution.

This transfer may be facilitated in particular by the fact that the deprotonated acid has a higher solubility in the second aqueous phase compared to the protonated acid. Therefore, this method step transfers the target molecule into an aqueous phase, where it is preferably purified or further concentrated.

In this method step as well, the second phase preferably has a smaller volume in the cathode chamber than the first phase. Preferably, this may already lead to a concentration or purification of the target molecule in the second phase compared to the first phase, but this is not mandatory for the invention.

The invention may particularly preferably provide that the aforementioned second embodiment of the method according to the invention is temporally downstream of the aforementioned first embodiment of the method according to the invention or both are performed simultaneously, wherein the second phase of one method step, in particular the method step performing the protonation, forms the first phase of the other method step, in particular the method step performing the deprotonation.

Thus, in this embodiment of this two-stage or parallel method, the target molecule (initially) present in aqueous solution, in particular by the protonation in the anode chamber, is transferred to this reactive extraction agent as a binding partner, for example by the formation of hydrogen bonds, and is then returned to an aqueous phase. As described above, this is preferably done in a dispersed state of the two phases.

The invention may provide that the two phases are left to settle before being separated. The second phase, in particular the formed complex of reactive extraction agent and target molecule, may then be transferred as a separated phase from the anode chamber into the cathode chamber for performing the second method step, in particular wherein the deprotonated target molecule is then transferred into the aqueous phase by the cleaving of the hydrogen bonds, which takes place during electrolysis, and deprotonation, in particular under the aforementioned different solubility conditions. Before the deprotonation is carried out in the cathode chamber, the anode chamber may already be filled again with two phases, so that extraction (for example with protonation) and back-extraction (for example with deprotonation) may be carried out simultaneously.

The arrangement in succession of the above-described method steps thus has the effect that the target molecule is transferred from an aqueous phase back into an aqueous phase, preferably with an increase in the concentration in the last aqueous phase.

A preferred development of this two-stage method, but also already of the aforementioned second embodiment of the method, in which a transfer into an aqueous phase is performed, may provide that the second phase, that is to say in particular the aqueous phase into which the target molecule was transferred in the aforementioned deprotonation step, is transferred into an anode chamber of an electrolysis unit.

This may be the anode chamber of any electrolysis unit, but preferably the anode chamber electrically associated with the cathode chamber in which the previously performed deprotonation step takes place.

It is then provided to crystallize the acid by lowering the pH value in the second aqueous phase by the performed electrolysis due to the pH-value-dependent solubility of the acid in water. The invention may further provide that the second phase separated from the crystallized acid is returned to the cathode chamber where the deprotonation step takes place. Thus, for example, the second phase may be circulated between these electrode chambers. Instead of using the specified acid, the crystallization step may also be carried out with other target molecules.

A further preferred embodiment may provide that the aforementioned anode chamber and the cathode chamber, which are mentioned with regard to the two method steps of protonation and deprotonation performed in succession or in parallel, are the electrode chambers of different electrolysis units.

Thus, for example, it is possible here that the previously described method step of the pH-value-dependent transfer (for example with protonation) of the target substance is performed by the anode chamber of a first electrolysis unit, wherein a pH-value adjustment of the first phase, from which the target substance was extracted, is performed in the cathode chamber of this electrolysis unit before this first phase is further used, for example the first phase that was removed from a fermentation reactor is returned to this reactor.

This therefore makes it possible to bring the pH value of the first phase remaining after extraction back to the original pH value of the first phase when it was removed from the fermentation reactor for extraction, or to increase it.

The aforementioned back-extraction of the target substance from the bound complex or organic solution back into the aqueous phase according to the second method step described above may thus be carried out with a cathode chamber of a second electrolysis unit. In the anode chamber of this electrolysis unit, the crystallization step may then preferably be carried out, which was also described above. The crystallized solid is then separated from the aqueous phase, the aqueous phase preferably being returned to a method cycle.

A possible embodiment may also provide for the omission of the previously described first electrolysis unit, for example if a fermentation in a fermentation reactor is already operated at a pH value at which the target molecule is present in protonated form. The fermentation broth of a fermentation reactor operated in this way may directly form a first aqueous phase from which the target molecule is extracted as previously described by dissolution or reactively. Thus, no electrolysis is required to adjust the pH value. In this case, the invention may, for example, provide only one electrolysis unit, in the cathode chamber of which the back-extraction is operated according to the previous description of the second embodiment and in the anode chamber of which a crystallization is operated according to the previously described development of the second embodiment.

The electrolysis processes performed inevitably produce oxygen and hydrogen. Here, the invention preferably provides that the oxygen created during electrolysis is used for the oxygen supply of a fermentation reactor.

In general, however, it may be provided to recycle the two gases created, by feeding them into a possible appropriate use, for example energy recovery or use in hydrogenation/hydro-formulation steps in further reaction steps of the method. The gases may also be stored in pressure vessels.

In general, according to a preferred embodiment of the invention, the target molecule is a saturated or unsaturated carboxylic acid having at least one carboxyl group that may be substituted, preferably with oxygen-containing functional groups. This may be an alkanoic acid with 1 to 4 carbon atoms, for example acetic acid or butyric acid, and/or an alkanedioic acid with 2 to 6 carbon atoms, for example oxalic acid, malonic acid, succinic acid, or adipic acid. Furthermore, this may be a (poly)hydroxyalkanoic acid with 2 to 6 carbon atoms, for example glycolic acid, lactic acid or gluconic acid, and/or an unsaturated alkanedioic acid with 2 to 6 carbon atoms, for example itaconic acid, or muconic acid. Furthermore, this may be an alkanoic acid with 4 to 6 carbon atoms with at least 2 carboxyl groups and at least 1 hydroxyl group, for example tartaric acid or citric acid. It is preferable to use, as water-soluble carboxylic acid, the carboxylic acids that are solid at temperatures of 20° C. and that may be precipitated during the back-extraction by targeted pH-value setting, preferably in crystalline form. Especially suitable for this purpose is itaconic acid and/or succinic acid and/or mixtures containing at least one of these carboxylic acids.

According to a further preferred embodiment of the invention, the target molecule is a water-soluble amine in the form of an alkylamine and -diamine with 2 to 6 linear or branched carbon atoms, for example 1-2-diethylenediamine and/or 1,6-diaminohexane.

According to a further preferred embodiment of the invention, the target molecule is a water-soluble amino acid selected from non-proteinogenic and/or proteinogenic amino acids According to a preferred embodiment of the invention, the target molecule is a water-soluble alkanediol having 1 to 7 carbon atoms, for example glycol, 1,2-propane glycol, 1,3-propanediol and/or 1,4-butanediol.

The aforementioned water-soluble amines, water-soluble amino acids, water-soluble alkanediols and/or water-soluble carboxylic acids are present in the target molecule either individually or as a mixture, preferably as a mixture.

According to a preferred embodiment of the invention, the binding partner is an aliphatic amine with at least 10 carbon atoms, which is primary, secondary or tertiary, the alkyl group(s) preferably having a total of 20 to 50 carbon atoms, and these being linear, cyclic or branched, for example tributylamine, trioctylamine, tridodecylamine and/or triocylamine-1-octanol. Tributylamine, trioctylamine and/or triocylamine-1-octanol are preferred.

According to a further preferred embodiment of the invention, the binding partner is an organophosphoric acid in the form of linear or branched alkyl phosphates having 2 to 3 alkyl groups, each alkyl group having 1 to 10 carbon atoms, for example tributyl phosphate and/or di-(2-ethylhexyl)phosphoric acid. Preferred is tributyl phosphate (TBP) and/or di-(2-ethylhexyl)phosphoric acid (D2EHPA).

According to a further preferred embodiment of the invention, the binding partner is a quaternary ammonium compound with at least 10 carbon atoms, for example cetyltriethylammonium (CTAB) and/or tetrabutylammonium hydroxide (TBAH).

The aforementioned aliphatic amines with at least 10 carbon atoms, organophosphoric acids with 2 to 3 alkyl groups, and quaternary ammonium salts are present in the binding partner either individually or as a mixture, preferably as a mixture.

The method according to the invention thus makes it possible particularly preferably to purify or concentrate fermentatively produced carboxylic acids, but is not limited to this application. Further applications are the pH-sensitive extraction of amino acids, amines or other ions of which the extractability depends on the pH value, for example a side group that may participate in an equilibrium reaction in a pH-value-dependent manner: for example a carboxy group, hydroxy group, or amino group (individually or in combinations).

A number of different carboxylic acids occurring in the aqueous phase may possibly be transferred from the aqueous phase to the other phase depending on the pH value created in the aqueous phase during the electrolysis. In this way, a selection of one or more acids from a number of acids may be made by a specific choice of the pH value during the electrolysis.

Last, the object of the invention is to use the previously described method of the recycling of fermentation residues from which target molecules may be enriched and isolated.

The invention therefore relates to the use of the above-described method of the enrichment and subsequent isolation of the above-described target molecule(s), in particular of saturated or unsaturated carboxylic acids having at least one carboxyl group that is optionally substituted, optionally with oxygen-containing functional groups, preferably by a pH-initiated precipitation.

BRIEF DESCRIPTION OF THE DRAWING

Embodiments of the invention are illustrated in the attached drawing and will be described below. In the drawing.

SPECIFIC DESCRIPTION OF THE INVENTION

Figure 1:
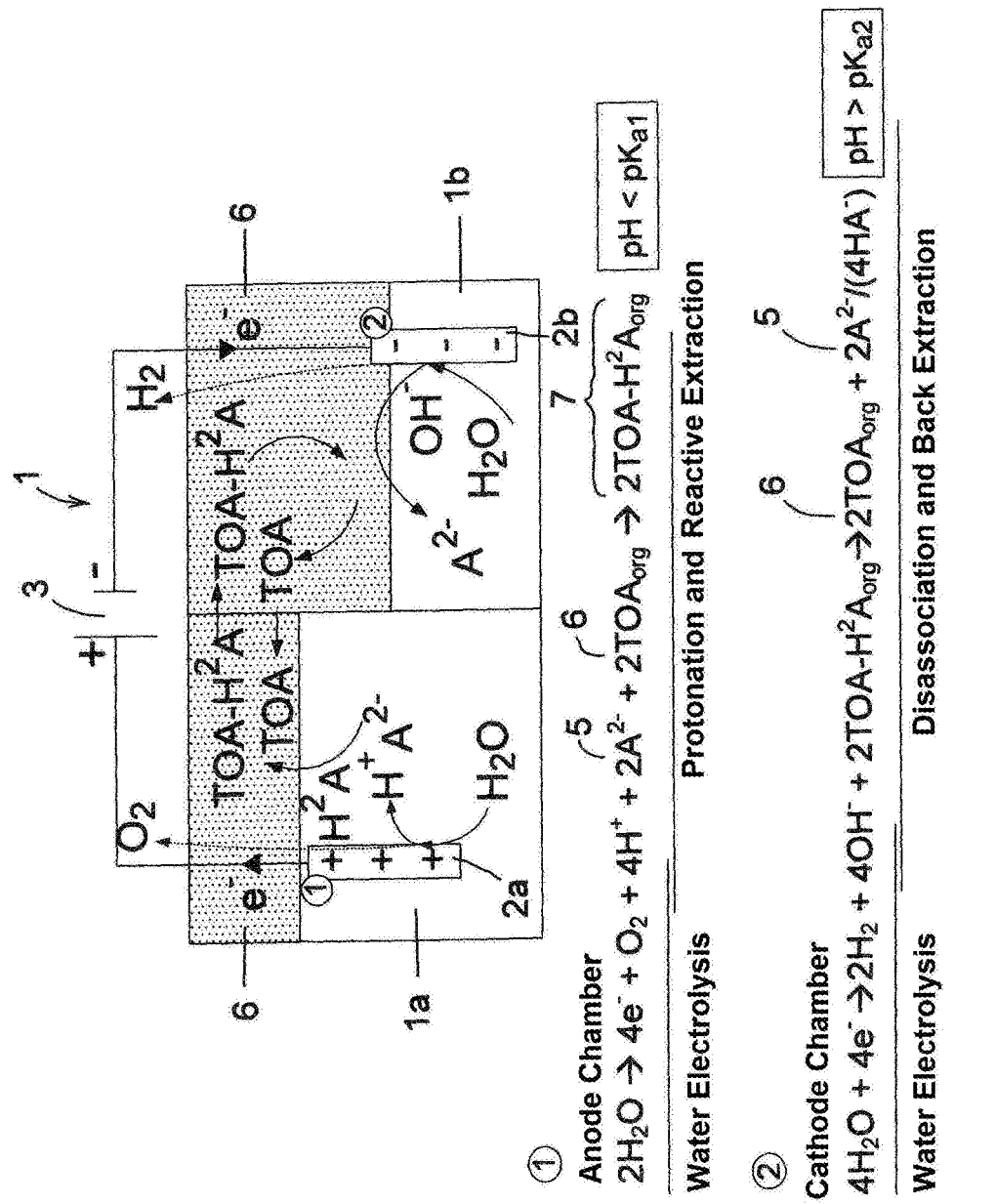
FIG. 1 is a diagram illustrating the invention.

FIG. 1 shows an electrolysis unit 1 with an anode chamber 1a and a cathode chamber 1b. The two chambers are separated in terms of the volumes thereof so that no unintentional convective exchange of the phases between the two chambers may take place. However, the chambers are connected to each other for charge carrier equalization, so that electrolysis may be performed via an anode 2a, a cathode 2b and a power supply 3.

In the anode chamber 1a there is an aqueous first phase 4 that comprises an acid 5 dissolved in water. When electrolysis is being performed, hydrogen ions (protons) are created at the anode, resulting in protonation of the acid 5 in the aqueous first phase 4 and the acid attaching itself to the reactive extraction agent 6 by hydrogen bonding that at the same time forms the second phase 6 or is at least contained in it. In this illustration, the two phases are shown one on top of the other and thus floating one on top of the other, which is merely symbolic for visualization of the phases. According to the invention, it is preferred to disperse the two phases 4 and 6 for the extraction to be performed, for example in the anode chamber 1a or even before.

The addition via the hydrogen bond therefore produces the complex 7 in the second phase 6 according to the first equation in FIG. 1. For example, the first phase 4 may be taken from a fermentation reactor to extract the acid formed by fermentation from this phase. The electrolysis causes a pH value shift below the acid number of this acid.

FIG. 1 shows exchange arrows in the upper region of the two electrode chambers between the opposite upper phases of the anode chamber 1a and cathode chamber 1b. This does not mean that these two chambers are connected to each other with regard to a possible material exchange, but that may be provided in accordance with the method to transfer this phase 6, for example convectively, into the cathode chamber 1b after an initial extraction of the acid 5 into the phase 6, in order to there carry out a back-extraction into an aqueous phase 8.

Then, in a subsequent step or, if necessary, a step that may also be performed in parallel, $OH^-$ ions are created by performing electrolysis in the cathode chamber 1b, which leads to deprotonation and breaking of the hydrogen bonds in phase 6, so that the acid 5 bound to the reactive extraction agent 6 is cleaved and deprotonated. Due to a higher solubility of the deprotonated acid 5 in the aqueous phase 8 of the cathode chamber 1b, the deprotonated acid dissolves and is enriched or concentrated there compared to the aqueous phase 4.

After cleaving, the phase 6 and thus the reactive extraction agent may be transferred back into the anode chamber 1a according to the arrows in order to perform the two method steps cyclically. During electrolysis, the pH value in the cathode chamber 1b is increased above the acid number of the aqueous solution, i.e. of the phase 8. In the cathode chamber as well, it is preferred to disperse the two phases 6 and 8 in order to obtain the largest possible surface area between the phases.

In the cathode chamber the reaction takes place according to equation 2 that shows that after electrolysis in this chamber performing the dissociation of the formed complex 7, the phase 6 corresponds substantially to the original reactive extraction agent.

Figure 2:
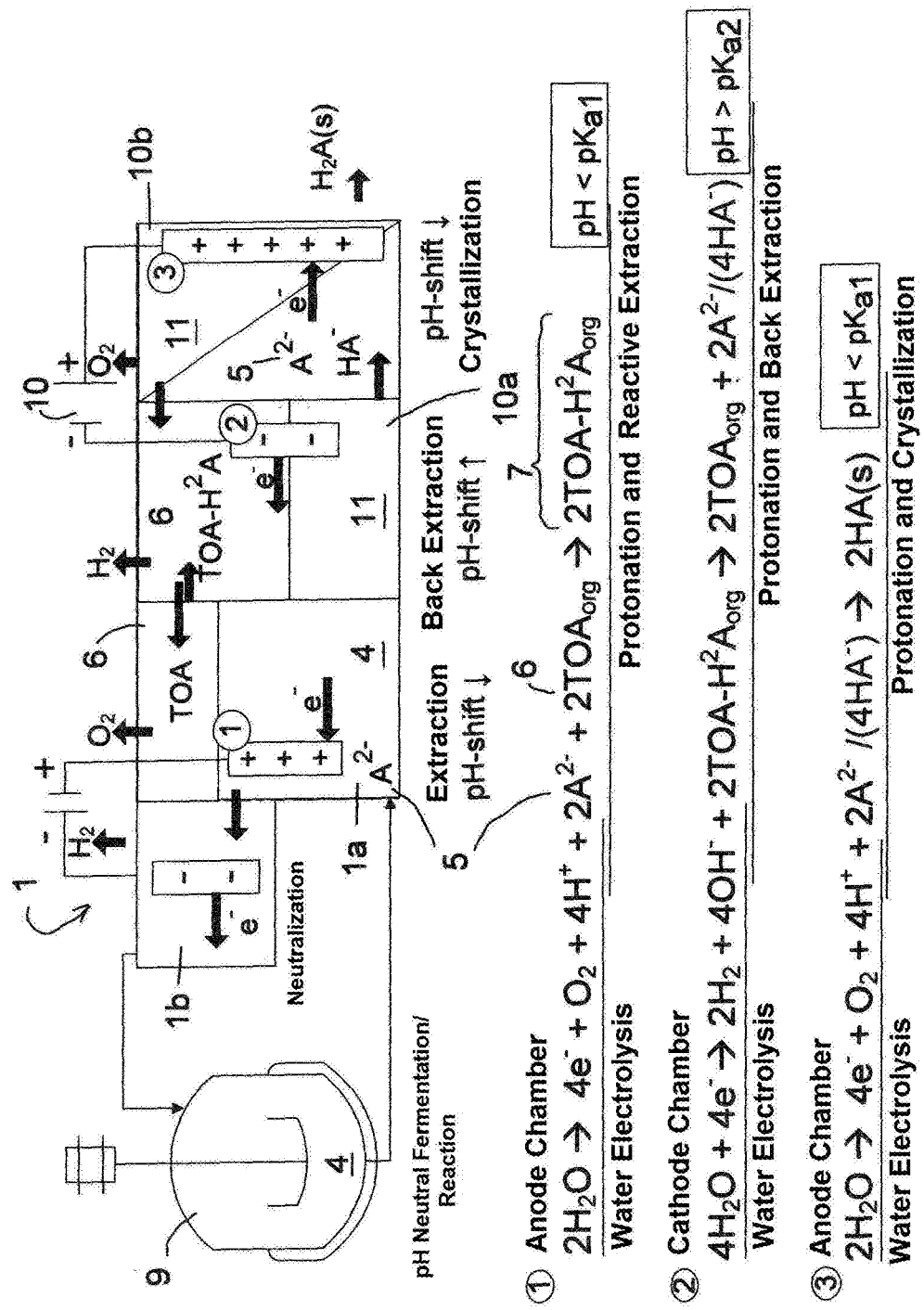
FIG. 2 is another diagram illustrating the invention.

FIG. 2 shows a further embodiment of the method of the extraction and crystallization of a fermentation acid from a fermentation reactor 9. This comprises a first phase 4 that is introduced through pipes into an anode chamber 1a of an electrolysis unit 1 and comprises the acid 5 in aqueous solution. As in the embodiment of FIG. 1, the reactive extraction agent 6 is provided as the second phase 6 in the anode chamber 1a, i.e. this phase is formed predominantly, if not entirely, by the pure reactive extraction agent 6.

In the anode chamber 1a, the very same protonation reaction takes place as described with reference to FIG. 1 and visualized by equation 1 at the bottom of FIG. 2, i.e. the acid 5 is attached to the reactive extraction agent 6 by protonation via hydrogen bonds in order to again form in this case as well the complex 7 formed by hydrogen bonds.

After this first extraction of the acid 5 into the second phase 6, FIG. 2 shows that the first phase 4, from which the acid is extracted, is fed back into the fermentation reactor 4 via the cathode chamber 1b, and electrolysis in the cathode chamber 1b causes the pH value of the aqueous phase 4, which is lowered during the protonation reaction, to be adjusted by the $OH^-$ ions in the cathode chamber before being fed back into the fermentation vessel 9, i.e. to be raised, preferably to the pH value that is present in the fermentation vessel 9. In this way the first phase 4 may be circulated between the fermentation vessel 9 and the anode chamber 1a.

The second step of the method described here involves transferring the phase 6 that now consists substantially of the complex 7 or at least predominantly comprises same, into a cathode chamber 10a of a second electrolysis unit 10.

In this cathode chamber 10a there is the transferred phase 6 as well as another phase 11, for example water or at least an aqueous phase comprising water. As a result of the $OH^-$ ion release taking place here, the acid 5 is cleaved from the complex 7 and the acid bound in the complex is deprotonated, so that the deprotonated acid 5 is transferred into the phase 11 due to its better solubility in water compared to the protonated acid and is enriched, i.e. concentrated, there. The phase 11 thus forms an aqueous phase in which the acid 5 is enriched compared to the aqueous phase 4.

FIG. 2 shows that the phase 6 is returned to the anode chamber 1a of electrolysis unit 1 after breaking up the complex 7 in order to be able to perform the extraction process repeatedly with this phase. The phase 11 concentrated with the acid 5 is transferred from the cathode chamber 10a of the electrolysis unit 10 to its anode chamber 10b, where in this aqueous phase 11 a pH value shift to lower pH values occurs due to the release of hydrogen ions in this chamber. Since the solubility of the acid 5 in the aqueous phase 11 is pH-value-dependent and, in particular, has a lower solubility at lower pH values than at higher pH values, the pH-value decrease in the anode chamber leads to crystallization of the acid.

The acid may thus be removed as a solid from the anode chamber 10b and, for example, may be routed to its desired application.

FIG. 2 shows that the phase 11 may be transferred back into the cathode chamber of the second electrolysis unit 10 after the process of crystallization in order to perform a back-extraction in the cycle, as described previously.

It is thus clear that the various phases 4, 6 and 11 may each be circulated. The extraction, back-extraction and crystallization may thus be carried out continuously.

The back-extraction in the cathode chamber 10a is carried out according to equation 2 below FIG. 2 and is thus identical to FIG. 1. The crystallization in the anode chamber is described by equation 3 of FIG. 2.

The following example describes the electrochemically initiated back-extraction of itaconic acid from trioctylamine and demonstrates its feasibility.

Test Description:

For the back-extraction, 20 ml TOA loaded with itaconic acid and 130 ml of 1M KCl solution are added to the cathode chamber, and 130 ml of 1M KCl solution are added to the anode chamber. As anode, a titanium sheet with 7.5 cm$^2$ active area is used, and as cathode a nickel sheet with 7.5 cm$^2$ active area is used. Both chambers are convectively separated from each other by a porous glass filter. Before starting the electrolysis, the system is dispersed for 25 min to determine the initial concentration. Before starting the electrolysis, a concentration of 17.3 g/l of itaconic acid and a pH value of 3.5 is measured in the aqueous phase of the cathode chamber. Subsequently, a current flow of 0.75 A is generated for 60 min by applying a voltage of 15-25 V. After completion of the electrolysis, the concentration of itaconic acid in the aqueous phase of the cathode chamber is 24.42 g/l and the pH value is 4.3. In the non-optimized test setup, a Faraday efficiency of the extraction of 51% of the extracted amount of itaconic acid relative to the maximum amount of acid extractable by the transferred charge carrier amount was achieved. The concentration of itaconic acid was measured by HPLC (Agilent Technologies 1100) on an organic acid resin column with RI and DAD detector.

In the following example, the electrochemically initiated back-extraction of succinic acid with trioctylamine-1-octanol is described and its feasibility demonstrated.

Extraction of Succinic Acid:

For the extraction, 160 g of 0.5 M K$_2$SO$_4$ solution with 10 g succinic acid and a pH value of 7 set by KOH are added into the anode chamber. At the same time, 200 g of 0.5 M K$_2$SO$_4$ solution with 1.5 g succinic acid are added into the cathode chamber. Then, 35 g trioctylamine-1-octanol with a ratio of 0.4:0.6% m are added into the anode chamber and brought into contact with the aqueous phase by stirring. A platinum-coated titanium electrode with 7.5 cm$^2$ active area is used as the anode, and a nickel sheet with 7.5 cm$^2$ active area is used as the cathode. Both chambers are convectively separated from each other by a porous glass filter. Before starting the electrolysis, the system is dispersed for 25 min to determine the initial concentration. Before starting the electrolysis, a concentration of 45.11 g/l succinic acid and a pH value of 7 is measured in the aqueous phase of the anode chamber.

Then, by applying a voltage of 15-25 V, a current flow of 0.57 A is generated for 325 min. After completion of the electrolysis, the concentration of succinic acid in the aqueous phase of the anode chamber is 33.40 g/l and the pH value is 4.84. In the non-optimized test setup, a Faraday efficiency of the extraction of 61% of the protonated substance amount of succinic acid was achieved relative to the maximum substance amount of acid that may be protonated due to the transferred charge carrier amount. The succinic acid concentration was measured by HPLC (Agilent Technologies 1100) on an Organic Acid Resin column with RI and DAD detector.

Back-Extraction:

For the back-extraction, 40 g of trioctylamine-1-octanol loaded with succinic acid in a ratio of 0.4:0.6% m and 160 g of 0.5 M K$_2$SO$_4$ solution are added into the cathode chamber and 200 g of 0.5 M K$_2$SO$_4$ solution are added into the anode chamber. A platinum-coated titanium electrode with 7.5 cm$^2$ active area is used as the anode, and a nickel sheet with 7.5 cm$^2$ active area is used as the cathode. Both chambers are convectively separated from each other by a porous glass filter. Before starting the electrolysis, the system is dispersed for 25 min to determine the initial concentration. Before starting the electrolysis, a concentration of 22.31 g/l succinic acid and a pH value of 2.76 is measured in the aqueous phase of the cathode chamber. Subsequently, a current flow of 0.4 A for 280 min is generated by applying a voltage of 15-20 V. After completion of the electrolysis, the concentration of succinic acid in the aqueous phase of the cathode chamber is 32.53 g/l and the pH value is 6.3.

The functionality is demonstrated by two tests relating to the crystallization of dicarboxylic acids (itaconic acid and succinic acid).

An itaconic acid solution with a pH value of 4.1 was prepared for the itaconic acid crystallization by adding potassium hydroxide solution (50% by weight) at a load of 0.32 $g_{IA}/g_{H2O}$. Then, electrolyte (EL) K$_2$SO$_4$ was added, resulting in a loading of 0.07 $g_{EL}/g_{H2O}$ in the phase. 180 ml of the aqueous phase was homogeneously mixed with a stirrer for 8.5 h. The electrolysis was carried out with a mixed metal anode made of titanium with a ruthenium oxide coating from Magenta Special Anodes B.V. and a nickel cathode at a voltage of 20-25 V. The temperature was kept constant at 15° C. with a Lauda E100 thermostat. The mass of crystalline itaconic acid and an optical image of the crystals in transmitted light with an Olympus BH-2 microscope with an Olympus DP25 camera and their purity are used to check the functionality. Additionally, efficiency parameters of the electrochemical system are given.

Figure 3A:
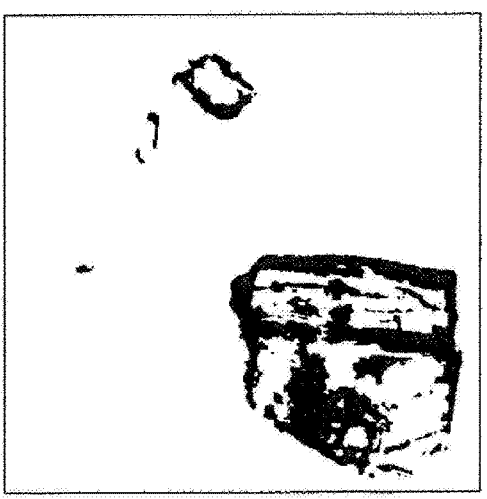
FIG. 3A-3C are photomicrographs illustrating the invention.
Figure 3B:
Figure 3C:
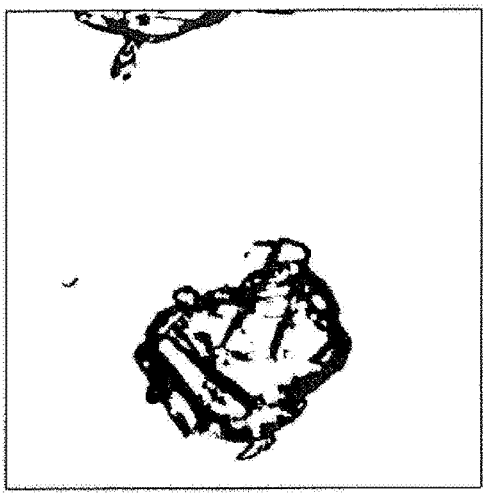

Result: 2.65 $g_{IA}$ could be recovered. Transmitted light microscope images are shown in FIGS. 3A through 3C. FIG. 3A shows a crystallizate magnified 40 times, FIGS. 3B and 3C show a crystallizate magnified 60 times. The specific current was on average 0.025 A/cm$^2$ with an anode-specific conversion of 0.031 g/cm$^2$ h. A Faraday efficiency of 43.74% was able to be achieved.

For the succinic acid crystallization, a succinic acid solution with a pH value of 4.144 was prepared by adding potassium hydroxide solution (50% by weight) at a load of 0.187 $g_{sA}/g_{H2O}$ Then, electrolyte (EL) K$_2$SO$_4$ was added, resulting in a loading of 0.033 $g_{EL}/g_{H2O}$ in the phase. 300 ml of the aqueous phase was homogeneously mixed with a stirrer for 2 h. The electrolysis was carried out with a mixed metal anode made of titanium with a ruthenium oxide coating from Magenta Special Anodes B.V. and a nickel cathode at a voltage of 20 V. The temperature was kept constant at 15° C. by the Lauda E100 thermostat. The mass of crystalline succinic acid and an optical image of the crystals in transmitted light with the Olympus BH-2 microscope with the Olympus DP25 camera and their purity are used to check the functionality. In addition, efficiency parameters of the electrochemical system are given.

Figure 4A:
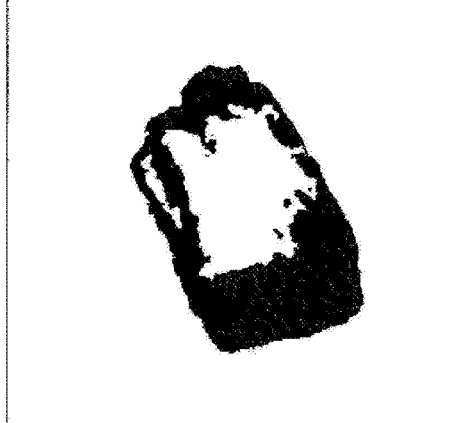
FIG. 4A-4C are further photomicrographs illustrating the invention.
Figure 4B:
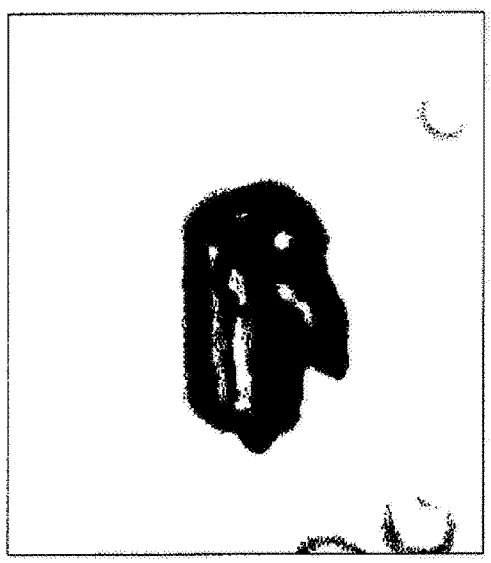
Figure 4C:
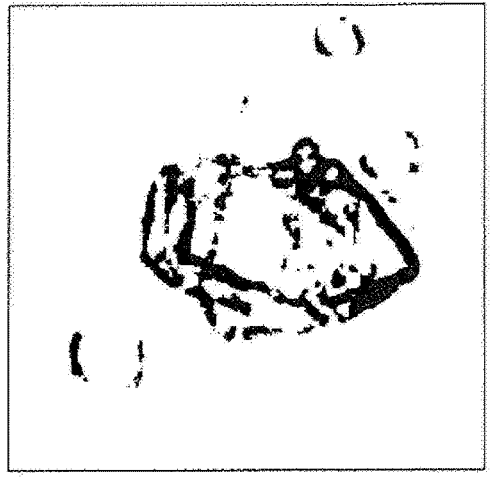

Result: 0.962 $g_{IA}$ could be obtained. Transmitted light microscope images are shown in FIG. 4. This shows the succinic acid crystallizate with 40× magnification. The purity of the crystals obtained corresponds to 89.4%. The average specific current was 0.034 A/cm$^2$ with an anode-specific conversion of 0.048 g/cm$^2$ h. A Faraday efficiency of 32.34% was able to be achieved.

The invention claimed is:

1. In a method of transferring a target substance between two liquid phases of which one phase is the target substance to be transferred and one other phase is an aqueous phase, the method comprising the steps of:

contacting both of the phases in one of two electrode chambers that are electrically conductively connected and are separated in terms of their volumes, thereafter generating a pH-value modification by H and/or OH ions created during the electrolysis in the aqueous phase and initiating with this modification a transfer of the target substance between the phases when the phases contact each other, the improvement wherein:

a) in a first step a first phase is formed by an aqueous solution of an acid as target molecule and a second phase contains a.i) a reactive extraction agent as binding partner and/or a.ii) an organic solvent, and the acid is protonated in the anode chambers of both electrode chambers and reactively adsorbs to the reactive extraction agent or goes into solution in the organic solvent in which the protonated acid has a higher solubility than the deprotonated acid and thereby is transferred from the first phase into the second phase, b) in a second step a first phase b.i) is formed by a complex of a reactive extraction agent as binding partner and a protonated acid bound thereto as target molecule or b.ii) is formed by an organic solvent in which a protonated acid is dissolved or, b.iii) is formed by a mixture of a reactive extraction agent and organic solvent to achieve one or both of the effects occurring in b.1 or b.ii and the second phase contains water, in the cathode chambers of the two electrode chambers the protonated acids are deprotonated and b.iv) cleaved by disrupting the bonds of the reactive extraction agent and/or b.v) goes into solution in the aqueous phase and thereby is transferred from the first phase into the second phase, c) the second method step b) being carried out after or simultaneously with the first method step a) and the second phase of the first method step a) forms the first phase of the method step b).

2. The method according to claim 1, wherein, by the aqueous electrolysis taking place between the electrode chambers, a) the target substance is protonated by the H ions created during the electrolysis or deprotonated by the OH ions created during the electrolysis, the transfer process being formed by the dissolution of the target substance in the respective phase of the two phases in which the target substance protonated by the electrolysis or the target substance deprotonated by the electrolysis has the higher solubility, or b) binding of the target substance to a binding partner in one of the phases or cleaving of the target substance from a binding partner in one of the phases is initiated by the created H+ and/or OH⁻ ions and/or by protonation/deprotonation of the target substance.

3. The method according to claim 1, wherein the target substance is a target molecule that is selected from the group of water-soluble amines, water-soluble amino acids, water-soluble alkanediols and/or water-soluble carboxylic acids.

4. The method according to claim 1, wherein the non-aqueous phase participating in the material exchange a) comprises an organic solvent selected from alcohols, esters, ketones, and aliphatic and aromatic hydrocarbons that are not miscible or are only partially miscible with the aqueous phase, b) comprises a reactive binding partner that, depending on the pH value, enters into reversible bonds with the target substance and that is selected from the group of aliphatic amines with at least 10 carbon atoms and organophosphoric acids with 2 to 3 alkyl groups.

5. The method according to claim 1, wherein the phases form a dispersion.

6. The method according to claim 1, wherein the first phase in the first method step a is taken from a fermentation reactor and, after performing the transfer of the target molecule to the second phase, is returned into the fermentation reactor via a cathode chamber electrically associated with the anode chamber during or after performance of the electrolysis.

7. The method according to claim 1, wherein the second phase is transferred in the second method step b) into an anode chamber of an electrolysis unit and, by lowering the pH value in the second phase by electrolysis carried out the acid is crystallized due to the pH-value dependent solubility of the acid in water.

8. The method according to claim 1, wherein the target molecule is transferred from an aqueous phase into an aqueous phase by the method step a) and b) performed in succession, with the concentration in the last aqueous phase being increased.

9. The method according to claim 1, wherein the anode chamber and the cathode chamber are electrode chambers of different electrolysis units.

10. The method according to claim 1, wherein oxygen created during an electrolysis process is used for the oxygen supply of a fermentation reactor.

11. The method according to claim 1, wherein the target molecule present in aqueous solution of the first phase has at least one pH-value-sensitive functional group which gives the target molecule a pH-dependent solubility and/or allows it to bind pH-dependently to the reactive agent.

12. The method according to claim 1, wherein the binding partner in the second phase is selected from aliphatic amines with at least 10 carbon atoms.

* * * * *